United States Patent
Chiu et al.

(10) Patent No.: US 6,371,120 B1
(45) Date of Patent: Apr. 16, 2002

(54) SNORE ELIMINATION DEVICE

(76) Inventors: Kuo-Chung Chiu; Wing-Yig Stephen Chan, both of No. 26, Alley 39, Lane 12, Cheng-kung St., A-Lein Hsiang, Kaohsiung Hsien (TW)

(*) Notice: Subject to any disclaimer, the term of this patent is extended or adjusted under 35 U.S.C. 154(b) by 0 days.

(21) Appl. No.: 09/880,677

(22) Filed: Jun. 15, 2001

(51) Int. Cl.[7] .................................................. A61F 5/56
(52) U.S. Cl. ...................................... 128/848; 602/902
(58) Field of Search ................................ 128/846, 848, 128/859–862; 602/902; 340/575

(56) References Cited

U.S. PATENT DOCUMENTS

| | | | | |
|---|---|---|---|---|
| 3,480,010 A | * | 11/1969 | Crossley | 128/848 |
| 3,998,209 A | * | 12/1976 | Macvaugh | 340/566 |
| 4,715,367 A | * | 12/1987 | Crossley | 128/136 |
| 5,081,447 A | * | 1/1992 | Echols | 340/573 |
| 5,458,105 A | * | 10/1995 | Taylor | 128/848 |

* cited by examiner

*Primary Examiner*—Michael A. Brown
(74) *Attorney, Agent, or Firm*—Charles E. Baxley

(57) ABSTRACT

A snore elimination device includes a base having a wrist belt so as to be connected to a user's wrist, and a cover is mounted on the base. A circuit board is received in the base and a power source is connected to the circuit board. A control arrangement is located on the circuit board and includes a sound magnifying circuit which magnifies the snores and sends the magnified snore to a sound transferring circuit which transfers the sound to a control circuit which activates a driving circuit and drives a vibration motor. The user receives the vibration and changes sleep poses.

4 Claims, 4 Drawing Sheets

SNORE ELIMINATION DEVICE

FIELD OF THE INVENTION

The present invention relates to a snore elimination device which is tied on user's wrist and includes a vibration motor which is activated by a driving circuit which is started when receiving snore. By the vibration to the user, the user will change his/her pose and stops snoring.

BACKGROUND OF THE INVENTION

Snoring is a symbol that warns a person that his/her health perhaps has problems. The sound generated from snoring is unstandable for the person who sleeps beside you. A device for eliminating snoring known to applicant employs minor electric shock to the user to change the sleep pose so as to obtain the result of stopping snoring. The device has to connect wires to the user's skin by using pads attached on the skin, and the pads are easily to disengage from the skin. Some users could be allergic to the attaching glue or the pads. The device uses electric shock to stimulate the user and such electric shock could be harmful to the users who has heart diseases or is pregnant.

The present invention intends to provide a snore elimination device that uses a vibration motor to stimulate the user to change his/her sleep poses.

SUMMARY OF THE INVENTION

In accordance with one aspect of the present invention, there is provided a snore elimination device which comprises a base having a wrist belt and a cover is mounted on the base. A circuit board is received in the base and a power source is connected to the circuit board. A control arrangement is located on the circuit board and comprises a sound magnifying circuit, sound transferring circuit, a control circuit, a driving circuit and charging circuit. A microphone is connected to the sound magnifying circuit and the sound transferring circuit transfers the sound into digital signals which are sent to the control circuit. The driving circuit is activated by the control circuit. A vibration device is activated by the driving circuit.

The primary object of the present invention is to provide a snore elimination device that is tied on the user's wrist and may vibrate the user's arm to change sleep poses.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
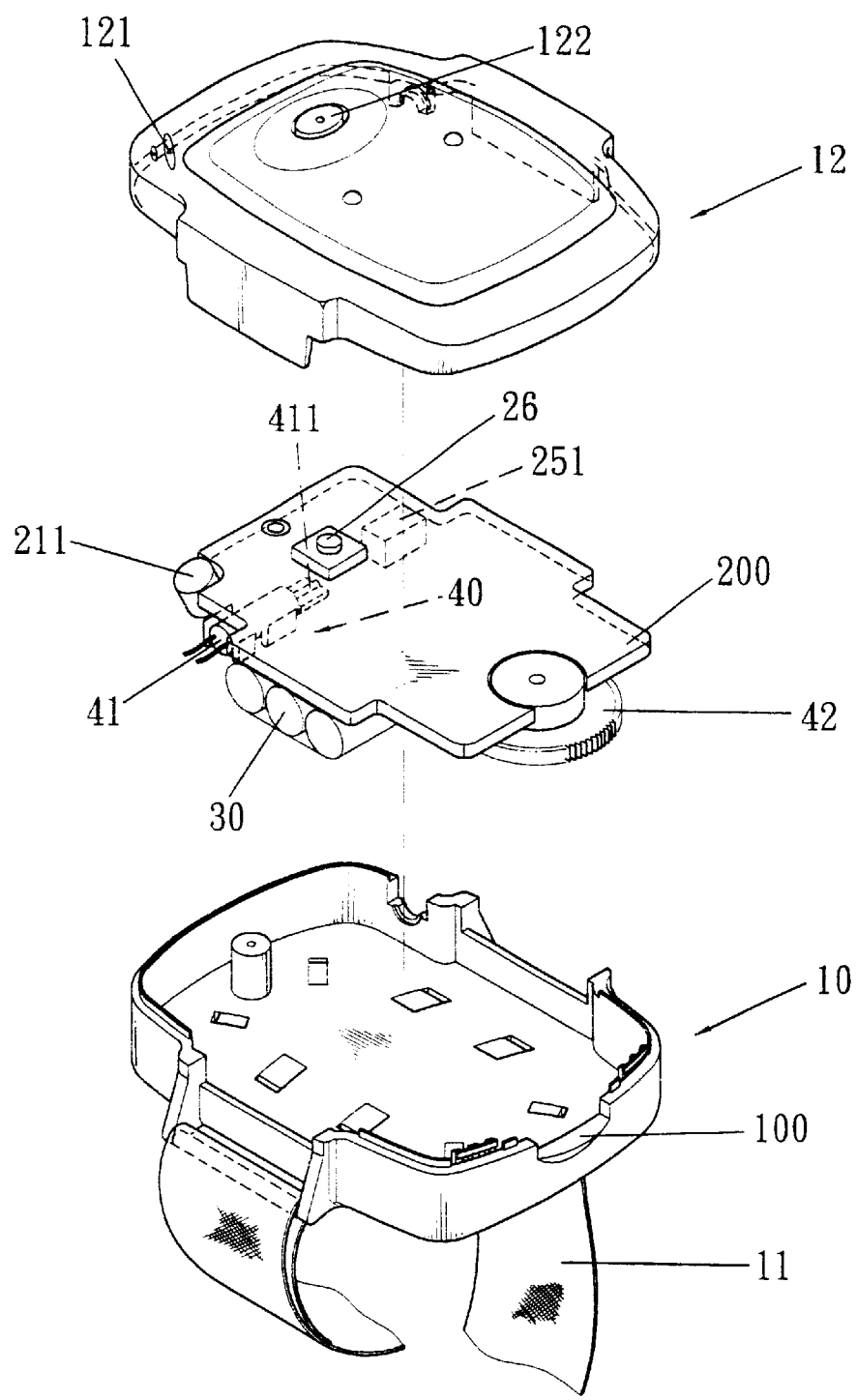
FIG. 1 is an exploded view to show a snore elimination device of the present invention.
Figure 2:
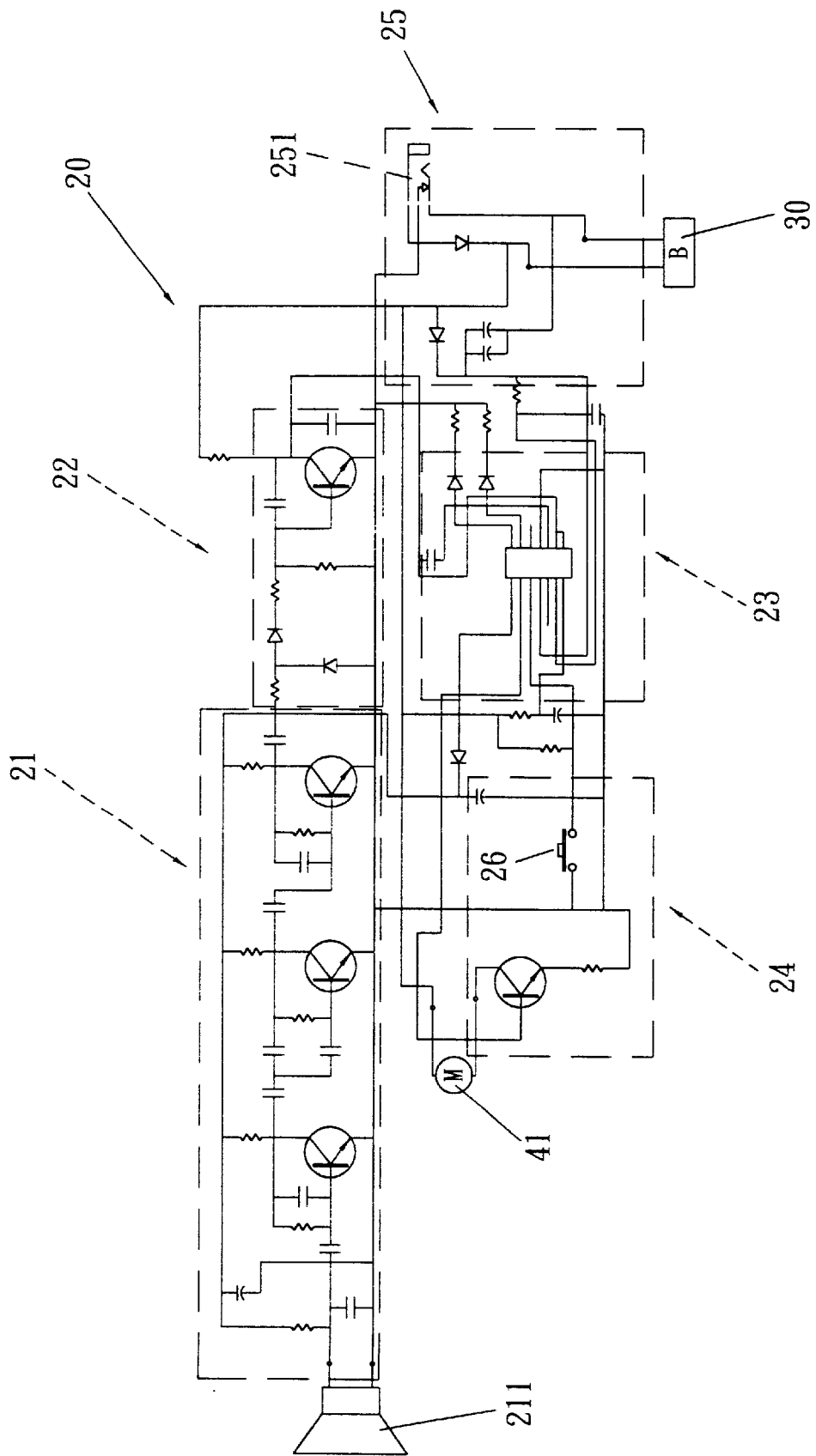
FIG. 2 is an illustrative view to show a circuit of the control arrangement of the snore elimination device of the present invention.
Figure 3:
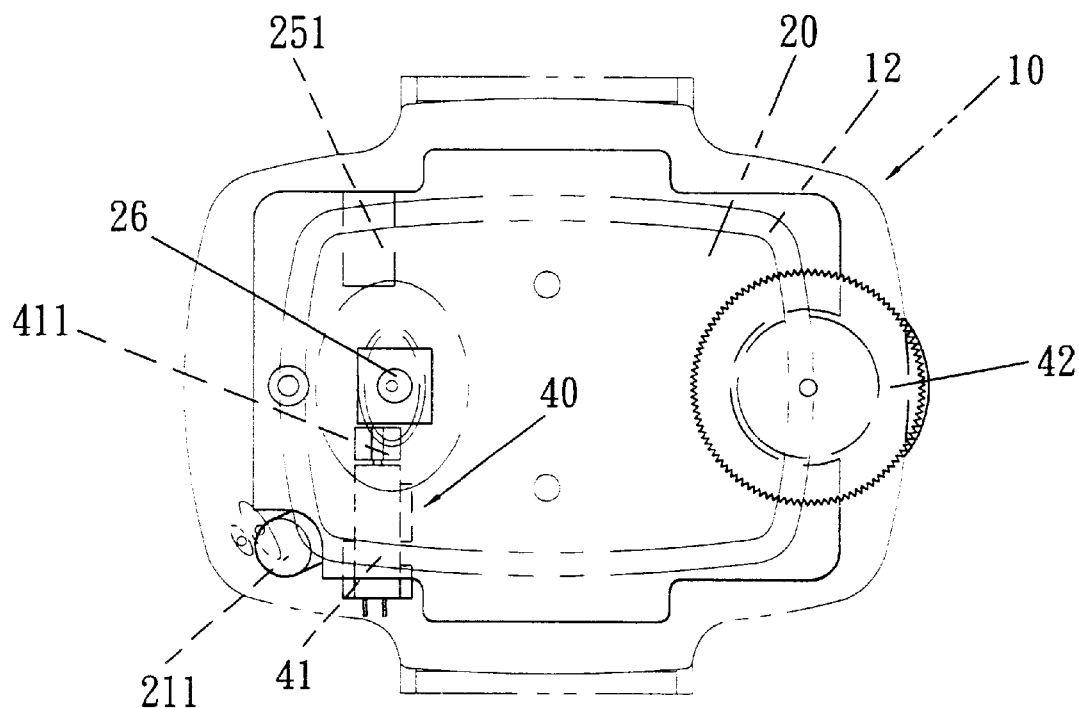
FIG. 3 is a plan view to show the parts of the snore elimination device of the present invention.
Figure 4:
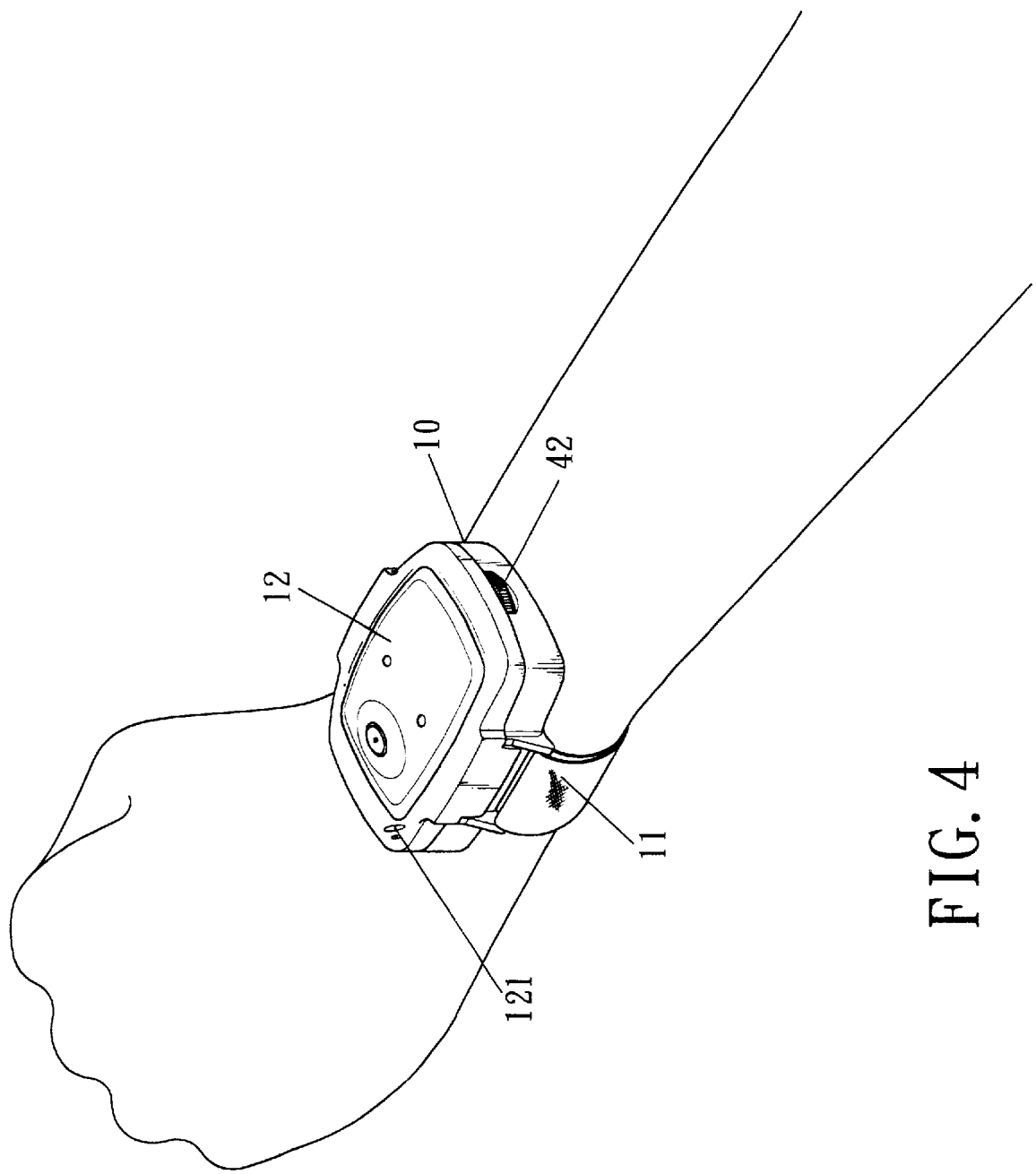
FIG. 4 is an illustrative view to show the snore elimination device of the present invention is tied on a user's wrist.

Referring to FIGS. 1 to 4, the snore elimination device of the present invention comprises a base 10 having a wrist belt 11 connected thereto so as to be tied on a user's wrist as shown in FIG. 4. A cover 12 is mounted on the base 10 and a circuit board 200 is received in the base 10 and a power source 30 is connected to the circuit board 200. A control arrangement 20 is located on the circuit board 200 and powered by the power source 30. The control arrangement 20 comprises a sound magnifying circuit 21, sound transferring circuit 22, a control circuit 23, a driving circuit 24 and a charging circuit 25. A microphone 211 is connected to the sound magnifying circuit 21 and the sound transferring circuit 22 transfers the sound of snore into digital signals which are then sent to the control circuit 23. The control circuit 23 activates the driving circuit 24 to drive a vibration device 41. The vibration device 41 is a vibration motor which has an eccentric block 411 so that the eccentric block 411 is rotated to vibrate the user's wrist to let the user to change his/her sleep poses. A receptacle 251 is connected to the circuit board 200 so as to charge the power source 30 from exterior.

The circuit board 200 has a adjustable member 42 which is accessed via a slot 100 defined in the base 10 and the vibration device 41 is connected to the adjustable member 42. The levels of the vibration of the vibration device 41 can be adjusted by rotating the adjustable member 42. The cover 12 has a plurality of holes 121 defined therethrough and the holes 121 are located correspondent to the microphone 211 so as to allow the microphone 211 to receive the snore. A switch 26 is located on the circuit board 200 and is pressed by pressing a button 122 on the cover 12 to activate the control arrangement 20.

The way to stimulate the user of the snore elimination device of the present invention is suitable for anyone.

While we have shown and described the embodiment in accordance with the present invention, it should be clear to those skilled in the art that further embodiments may be made without departing from the scope of the present invention.

What is claimed is:

1. A snore elimination device comprising:

a base having a wrist belt connected thereto and a cover mounted on said base;

a circuit board received in said base and a power source connected to said circuit board, a control arrangement located on said circuit board and powered by said power source, said control arrangement comprising a sound magnifying circuit, a sound transferring circuit, a control circuit, a driving circuit and a charging circuit, a microphone connected to said sound magnifying circuit and said sound transferring circuit transferring said sound into digital signals which are sent to said control circuit, said driving circuit being activated by said control circuit, and a vibration device activated by said driving circuit.

2. The device as claimed in claim 1, wherein said circuit board has a adjustable member which is accessed via a slot defined in said base and said vibration device is connected to said adjustable member.

3. The device as claimed in claim 1, wherein said cover has a plurality of holes defined therethrough and said holes are located correspondent to said microphone.

4. The device as claimed in claim 1 wherein said vibration device is a vibration motor which has an eccentric block.

* * * * *